United States Patent [19]

Jess et al.

[11] 4,217,993
[45] Aug. 19, 1980

[54] FLOW METERING APPARATUS FOR A FLUID INFUSION SYSTEM

[75] Inventors: Thurman S. Jess, Mundelein; Norm Shim, Glenview, both of Ill.

[73] Assignee: Baxter Travenol Laboratories, Inc., Deerfield, Ill.

[21] Appl. No.: 856,863

[22] Filed: Dec. 2, 1977

[51] Int. Cl.$^2$ .......................................... A61M 31/31
[52] U.S. Cl. ....................................... 222/14; 222/63; 128/214 E; 128/DIG. 13
[58] Field of Search ................... 222/14–22, 222/63, 71; 128/214 E, 214 F, DIG. 12, DIG. 13

[56] References Cited

U.S. PATENT DOCUMENTS

| | | | |
|---|---|---|---|
| 2,835,252 | 5/1958 | Mauchel | 128/214 E |
| 3,736,930 | 6/1973 | Georgi | 222/14 X |
| 3,737,251 | 6/1973 | Berman et al. | 128/214 F X |
| 3,764,783 | 10/1973 | Terry et al. | 235/92 EV |
| 3,887,110 | 6/1975 | Porter | 222/16 |
| 3,985,266 | 10/1976 | Wright | 222/22 |
| 3,989,913 | 11/1976 | Lundquist et al. | 128/214 E X |
| 4,036,431 | 7/1977 | Gidlof | 235/92 PE |
| 4,094,318 | 6/1978 | Burke et al. | 128/214 E |

Primary Examiner—Joseph J. Rolla
Attorney, Agent, or Firm—Paul C. Flattery; John P. Kirby, Jr.; Eugene M. Cummings

[57] ABSTRACT

A system for infusing fluids into the human body includes a peristaltic-type metering apparatus which controls the flow of fluid through a disposable administration set. The metering apparatus includes a control system which allows the volume and rate of flow of the fluid to be infused to be accurately preset by the operator. The control system provides an alarm function in the event of malfunction of the pump or occlusion of the tubing of the administration set, and a minimum pumping rate for maintaining fluid flow through the system after the desired volume of fluid has been infused. Novel power supply circuitry within the control system renders the system immune to power line transients, and a novel bubble detector circuit provides for more reliable detection of air bubbles in the tubing. A mechanical linkage between the pressure plate and downline flow restriction plunger of the metering apparatus provides for convenient loading of the administration set and for automatic closure of the plunger prior to use.

11 Claims, 14 Drawing Figures

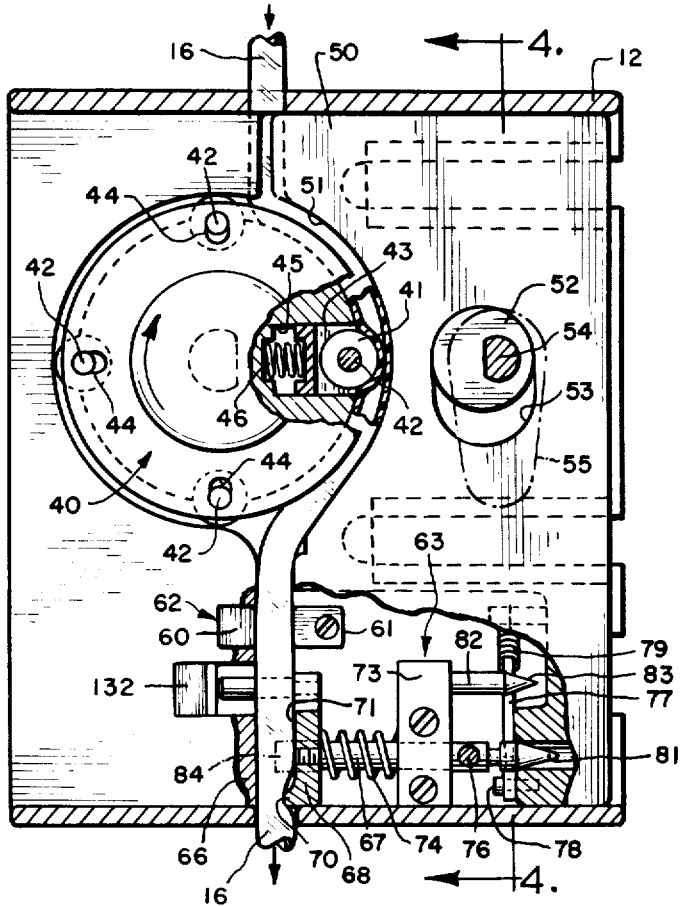
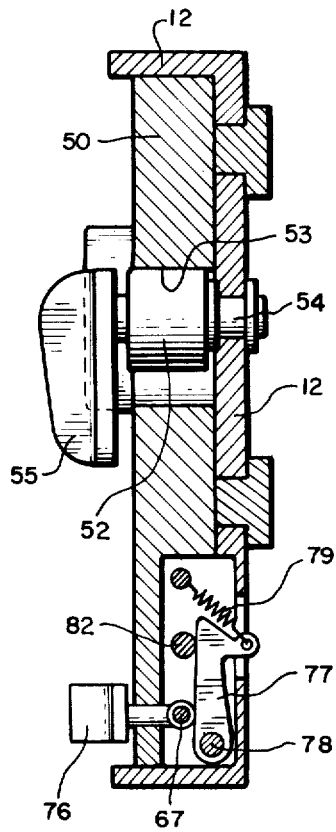
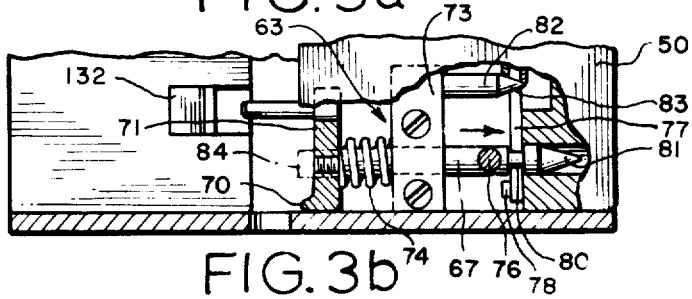
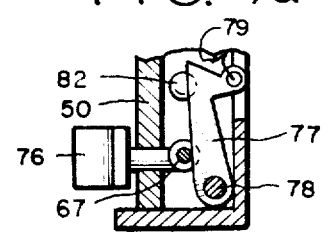
FIG. 3
FIG. 4
FIG. 3a
FIG. 4a
FIG. 3b
FIG. 4b

FLOW METERING APPARATUS FOR A FLUID INFUSION SYSTEM

BACKGROUND OF THE INVENTION

The present invention relates generally to fluid infusion systems, and more particularly to an improved flow metering apparatus for such systems.

The infusion of fluids into the human body is usually accomplished by means of an administration set in conjunction with metering apparatus which controls the rate of flow of fluid through the set. Peristaltic-type pumps, which function by repetitively compressing and expanding a section of tubing, have proven particularly attractive for use in metering apparatus since they do not introduce the possibility of leakage or contamination into the system, while providing positive control of fluid flow through the system.

One form of peristaltic-type pump which is particularly well adapted for infusion applications is described in the co-pending application of Thurman S. Jess, Ser. No. 759,178, filed Jan. 13, 1977, now U.S. Pat. No. 4,155,362. Basically, this pump construction includes individually spring-biased rollers in the pump rotor which provide a uniform compression force, and a spring-biased plunger which restricts the lumen of the administration set downline of the pump rotor to provide a back pressure against which the pump must work. This prevents the release of dissolved gas in the tubing section, assists in restoring the tubing to its original shape following compression by the pump, and prevents uncontrolled gravity flow in the event of pump failure.

In many applications, such as where medication is being administered, it is necessary that the operation of the peristaltic pump be precisely controlled to infuse only a predetermined volume of fluid at a predetermined rate. Thus, the need has developed for a control system for peristaltic-type infusion pumps which enables the operator to preset a quantity and rate of infusion, and which continuously monitors the performance of the pump to insure compliance with the preset parameters by interrupting operation and alerting the operator in the event of a malfunction. Furthermore, it is desirable that the system be fail-safe, and substantially unaffected in operation or accuracy by power line interruptions or transients. The metering apparatus of the present invention provides these features in an integrated unit which is simple and convenient to use.

Accordingly, it is a general object of the present invention to provide a new and improved system for infusing fluids into the human body.

It is a more specific object of the present invention to provide a new and improved metering apparatus for use in conjunction with an administration set for infusing fluids into the human body.

It is another object of the present invention to provide a peristaltic-type pump and control system which provides for accurate administration of a predetermined quantity of fluid at a predetermined rate.

It is another object of the present invention to provide a fluid metering apparatus which provides improved metering accuracy and protection against malfunction.

It is another object of the invention to provide a self-contained fluid metering apparatus which is simple and convenient to use.

SUMMARY OF THE INVENTION

The invention is directed to metering apparatus for controlling the flow of fluid through a fluid infusion set. The metering apparatus includes a housing, a rotor mounted on the housing for rotation about a fixed axis and having a plurality of circumferentially-disposed pressure rollers, and a pressure plate for positioning a tubing segment of the administration set in compressive engagement with the rollers whereby fluid is pumped through the tubing segment with rotation of the rotor. Means including a stepper motor are provided for driving the rotor. The stepper motor is driven by a first source of stepper pulses at a user-adjustable rate, or by a second source of pulses at a fixed minimum rate when a predetermined volume of fluid has been infused. Inhibiting means prevent operation of the minimum rate when the user-selected rate is above a predetermined maximum level.

The invention is further directed to the use of a bidirectional counter in the apparatus which counts down from a user-preset counting state to zero at which time infusion is terminated.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 3 is an enlarged front elevational view of the peristaltic pump utilized in the metering apparatus of FIG. 1 broken away to show the rotor and downline occlusion stations thereof.

FIGS. 3a and 3b show the downline occlusion station of the pump as seen in FIG. 3 in alternate positions.

FIG. 4 is a cross-sectional view of the pump taken along line 4—4 of FIG. 3.

FIGS. 4a and 4b show the latch member of the downline occlusion station as shown in FIG. 4 in alternate positions.

DESCRIPTION OF THE PREFERRED EMBODIMENT

Figure 1:
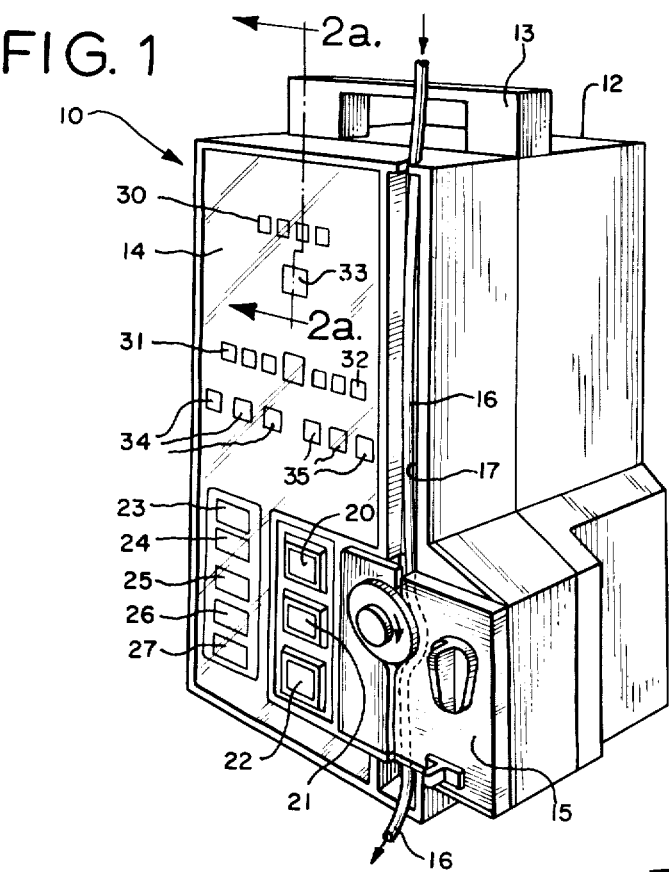
FIG. 1 is a perspective view of an infusion metering apparatus constructed in accordance with the invention.

Referring to the Figures, and particularly to FIG. 1, a peristaltic-type flow metering system 10 for use in conjunction with an administration set for controlling the flow of fluid into a vein or artery includes a generally rectangular housing 12 having a handle 13 at one end thereof for convenient carrying. The front surface of the housing includes a control panel 14 which allows the operator to control and monitor the operation of the metering apparatus, and a peristaltic-type flow metering head 15 for compressing a section of tubing 16 of the administration set to effect control of fluid flow therein. A channel 17 is provided above the metering head 15 for maintaining a portion of the tubing segment in a convenient view of the operator whereby flow irregularities can be more readily observed.

The administration set, of which tubing segment 16 is a part, and which may be conventional in design and construction, is preferably formed of a plastic material such as vinyl and packaged in a sterile and non-pyrogenic condition. To avoid the danger of contamination, the administration set is normally utilized for one application only, and is disposed of after use.

The operating mode of the metering apparatus is controlled by means of a push button STOP switch 20, a push button START switch 21, and a push button power ON-OFF switch 22. Each of these push button switches includes an internal indicator lamp which provides a positive indication of the operating mode of the apparatus.

Various abnormal operating conditions are annunciated by means of indicator lights 23-27 contained on the control panel to the left (as viewed in FIG. 1) of the mode control push buttons. The operation of these indicator lights will be explained in conjunction with the operation of their respective systems within the metering apparatus.

Control panel 14 further includes a digital display 30 of volume infused, a digital display 31 of volume to be infused, and a digital display 32 of the fluid flow rate. The volume displayed by display 30 is the volume of fluid actually infused, and can be reset to 0 by the operator by means of a push botton RESET switch 33. The volume to be infused by display 31 is preset by the operator by means of a set of push button switches 34 to indicate a desired volume of fluid to be infused. Similarly, the infusion rate display 32 is preset by the operator by means of a second set of push button switches 35 to indicate the rate at which infusion is to take place.

Figure 2A:
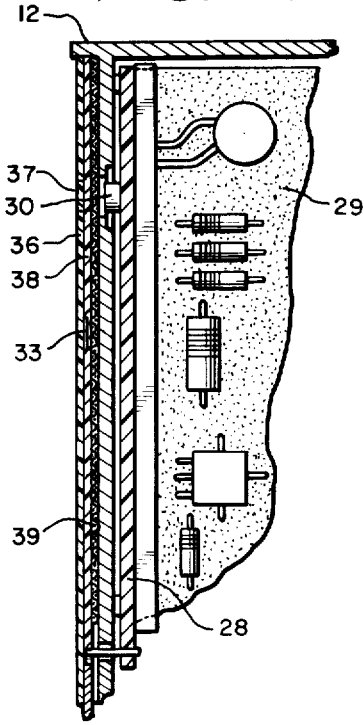
FIG. 2a is a cross-sectional view of the metering apparatus taken along line 2a—2a of FIG. 1.
Figure 2:
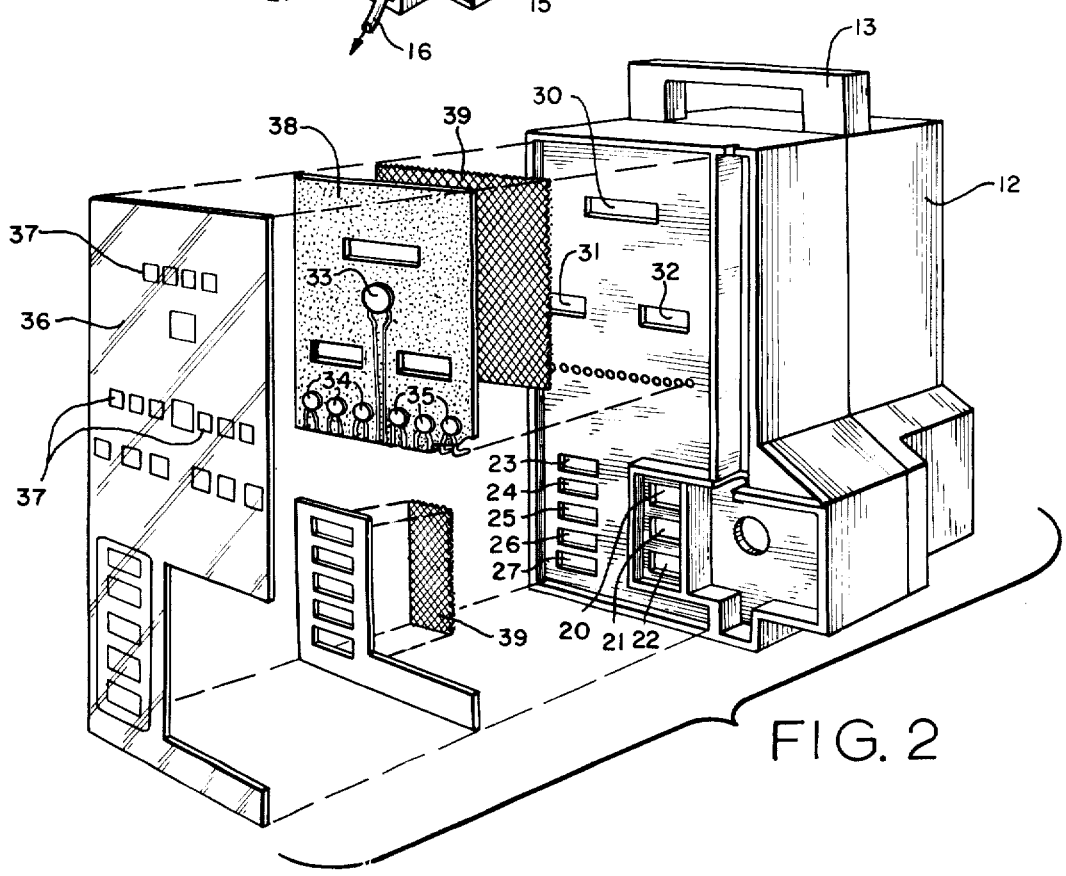
FIG. 2 is an exploded perspective view showing the principal components of the metering apparatus housing.

As shown in FIGS. 2 and 2a, to provide an aesthetically pleasing front panel surface free of openings which might harbor contaminants, the front panel 14 is preferably constructed from a single seamless panel 36 having necessary transparent sections 37 for viewing readouts 30, 31 and 32. The push button switches 33—35 associated with these displays and preferably pressure-sensitive switches, which respond to very small deformations of the front panel brought about by finger pressure from the operator to actuate their respective circuits. The pressure-sensitive switches are mounted on one side of a printed wiring board 38 behind panel 36, with connections from the board extending through apertures in the housing to a printed wiring board 28 within the housing. Additional individual system wiring boards 29 are plugged into sockets contained on this board. A plurality of metallic screen panels 39 may be provided between board 38 and housing 12 for the purpose of providing radio frequency interference (RFI) shielding for the electronic circuitry of the metering apparatus.

Referring to FIG. 3, the peristaltic metering head 15 includes a rotor 40 having four pressure rollers 41 disposed in equi-spaced relation about its circumference. The rollers are each mounted on a shaft 42 for free rotation thereon, and the shafts are carried on carriages 43 and constrained to radial movement by respective radial slots 44. Each carriage 43 is mounted for reciprocation within a radially aligned recess 45 and spring loaded in a radially outward direction by a helical spring 46 disposed within the recess.

The pump also includes a pressure plate 50 having an arcuate working surface 51 which substantially corresponds in shape to the circumference of the pump rotor and is positioned to bring the tubing segment 16 into compressive engagement with rollers 41 around at least a portion of the rotor circumference extending between adjacent rollers. The pressure plate may be reciprocated toward and away from rotor 40 to facilitate installation and removal of tubing segment 16 by rotation of an eccentric cam 52, which is constrained to operate within a vertical slot 53 provided on the pressure plate. Rotation of the cam is accomplished by a shaft 54 and user-actuable lever 55 operatively connected to the cam. When the lever 55 is in its bottom position, as shown in FIG. 3, the pressure plate is moved sufficiently close to the rotor circumference to cause tubing segment 16 to be completely occluded by the rollers. Since each of rollers 41 is individually biased into engagement with the tubing segment, the pressure applied by each roller is independent of the number of rollers engaging the tubing segment.

After passing through the peristaltic metering station, tubing segment 16 extends between a light source 60 and a photodetector 61, which together comprise a bubble detector station 62. As will be seen presently, it is the function of this station to discontinue operation and alert the operator upon formation of a bubble in the tubing segment.

Figure 5:
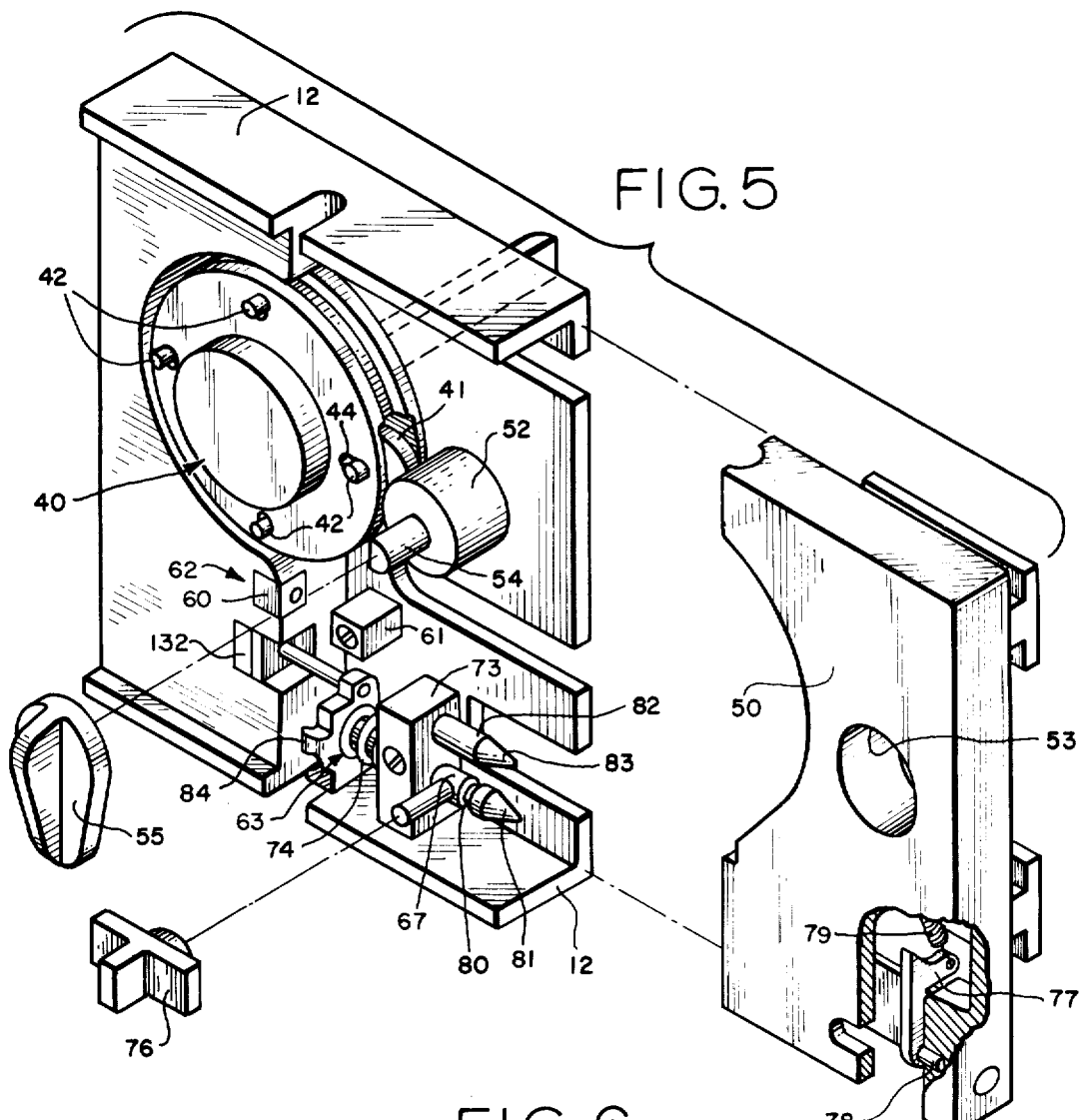
FIG. 5 is an enlarged exploded perspective view of the principal components of the fluid metering station of the metering apparatus.

Referring to FIGS. 3-5, the tubing next passes through a flow restriction station 63. This station includes a pressure block 66 and a slidably mounted flow restriction plunger 67 biased against the sidewall of tubing segment 16. The end of plunger 67 which engages the tubing segment includes a generally L-shaped head portion 68 having a wedge-shaped working surface 70 and a generally flat control surface 71. Plunger 67 includes a central body portion which is slidably received within a stationary mounting block 73, and which extends through the center of a helical compression spring 74 provided for biasing head 68 into engagement with tubing segment 16.

The working surface 70 of head portion 68 bears against the sidewall of tubing segment 16 substantially perpendicular to the direction of fluid flow within the tubing as the tubing is held in position against pressure block 66. As a result, the lumen of the tubing segment is occluded at the point of engagement, and a downline conduit segment is defined between the point of engagement of the rollers 41 and the point of engagement of the wedgeshaped working surface 70. As previously developed, the occlusion of the tubing in this way increases the pressure of the fluid in the tubing segment and prevents separation of dissolved gases therein.

The control surface 71 of plunger 67 extends substantially parallel to the direction of fluid flow and is substantially greater an area than the working surface 70. The relatively large area of the control surface 71 renders the plunger more sensitive to pressures in the tubing lumen when the pump is operative so that higher pressures can be exerted by spring 74 to more positively close off the tubing when the pump is not in operation, without detriment to its ability to open at lower operating pressures.

Plunger 67 may be opened to facilitate loading or unloading of tubing segment 16 by means of a user-actuated lever 76 mounted for reciprocation with plunger 67. The plunger is constrained to reciprocation along a defined operating path by the stationary mounting block 73 which is mounted to the apparatus housing 14. The helical compression spring bears against this mounting block at one end and against the head of the plunger at its other end, causing the desired bias of the plunger against the tubing segment.

Automatic release of the plunger is obtained by means of a latch member 77 which is pivotably mounted at 78 to pressure plate 50 and biased by a helical spring 79 for operation within a plane perpendicular to the plunger. The plunger includes a slot 80 in which the latch member 77 is received when the plunger is moved to its full open position, as shown in FIG. 3b. The end 81 of the plunger may be tapered to facilitate displacement of the latch member prior to seating in slot 80. Once the latch member has been received in the slot, the plunger is locked open and the tubing segment 16 can be readily removed.

To insure that plunger 67 will be released when pressure plate 50 is subsequently closed, mounting block 73 is provided with an actuator pin 82. As shown in FIGS. 3 and 4, this actuator pin has a tapered end surface 83 which serves to displace the pivotably mounted latch member 77 from slot 80 when the pressure plate is returned to its closed position by rotation of knob 55. In this way, the plunger is automatically released so as to again become spring-biased against the administration set tubing segment 16 as the metering station is closed. This prevents inadvertent operation of the system without the back pressure and gravity flow protection provided by the plunger. Also, when the pressure plate is open, the displacement of latching member 77 prevents the plunger from being latched open. A gate member 84 adjacent the control surface 71 of plunger 67 prevents the tubing segment from being inadvertently pulled free of the compression plunger during operation.

By reason of the tubing segment 16 being held in a highly visible vertical position within channel 17 the flow of fluid therethrough can be readily monitored. Furthermore, this channel obviates the need for additional tubing clamps at the inlet and outlet portions of metering head 15 while at the same time providing an aesthetically pleasing structure on the pump housing.

Figure 6:
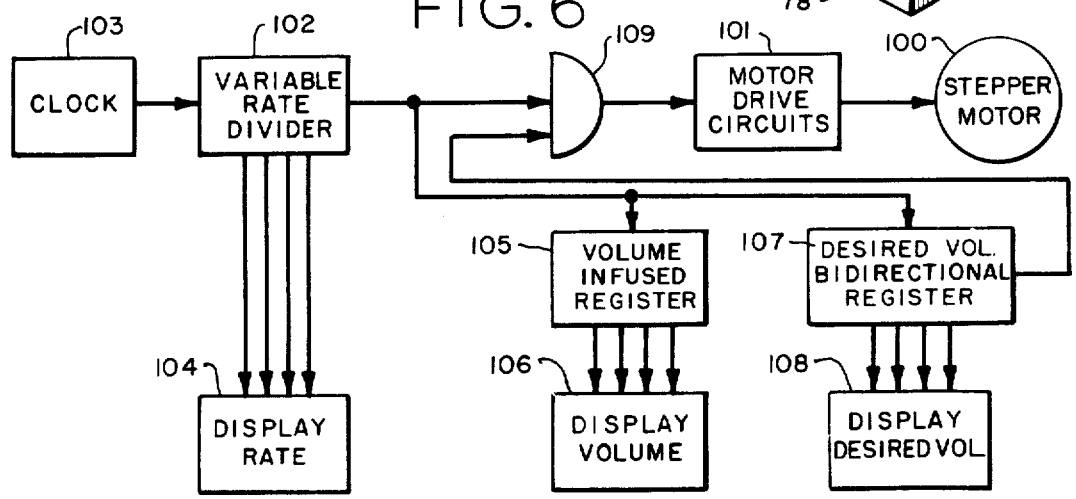
FIG. 6 is a simplified functional block diagram of the control system incorporated in the metering apparatus of the invention.

Referring now to FIG. 6, the control system for metering apparatus 12 is seen to include a stepper motor 100 which is rotatably coupled to rotor 40 so as to drive the rotor one increment for each step command applied to the motor. To supply the multi-phase signals required for operation of the stepper motor the metering apparatus includes multi-phase motor drive circuits 101 which respond to an applied control pulse to generate a multi-phase output signal which steps the motor one increment. The control pulses are generated by a variable rate divider 102 which produces an output signal after a predetermined number of input pulses have been received from a continuously running clock 103. The divider, which may be conventional in design and construction, is preset by the user to a desired division rate which is displayed by an associated display device 104. In this way, by setting different division factors into the variable rate diviser 102, the stepper motor can be operated over a wide range of rotational speeds.

To provide a display indicative of the total volume of fluid infused a register 105 responsive to the output pulses from divider 102 is provided. The counting state of register 105, and hence the volume infused, is displayed by a display device 106. The output pulses from divider 102 are also applied to a register 107 having an associated display device 108. This register is a bi-directional register, which prior to use of the metering apparatus is counted up to a counting state corresponding to the quantity of fluid to be infused, and then during use is counted down with infusion of the fluid until a zero counting state is reached. At this time the register generates an output signal which disables a gate 109 to interrupt application of control pulses to motor drive circuits 101.

Figure 7:
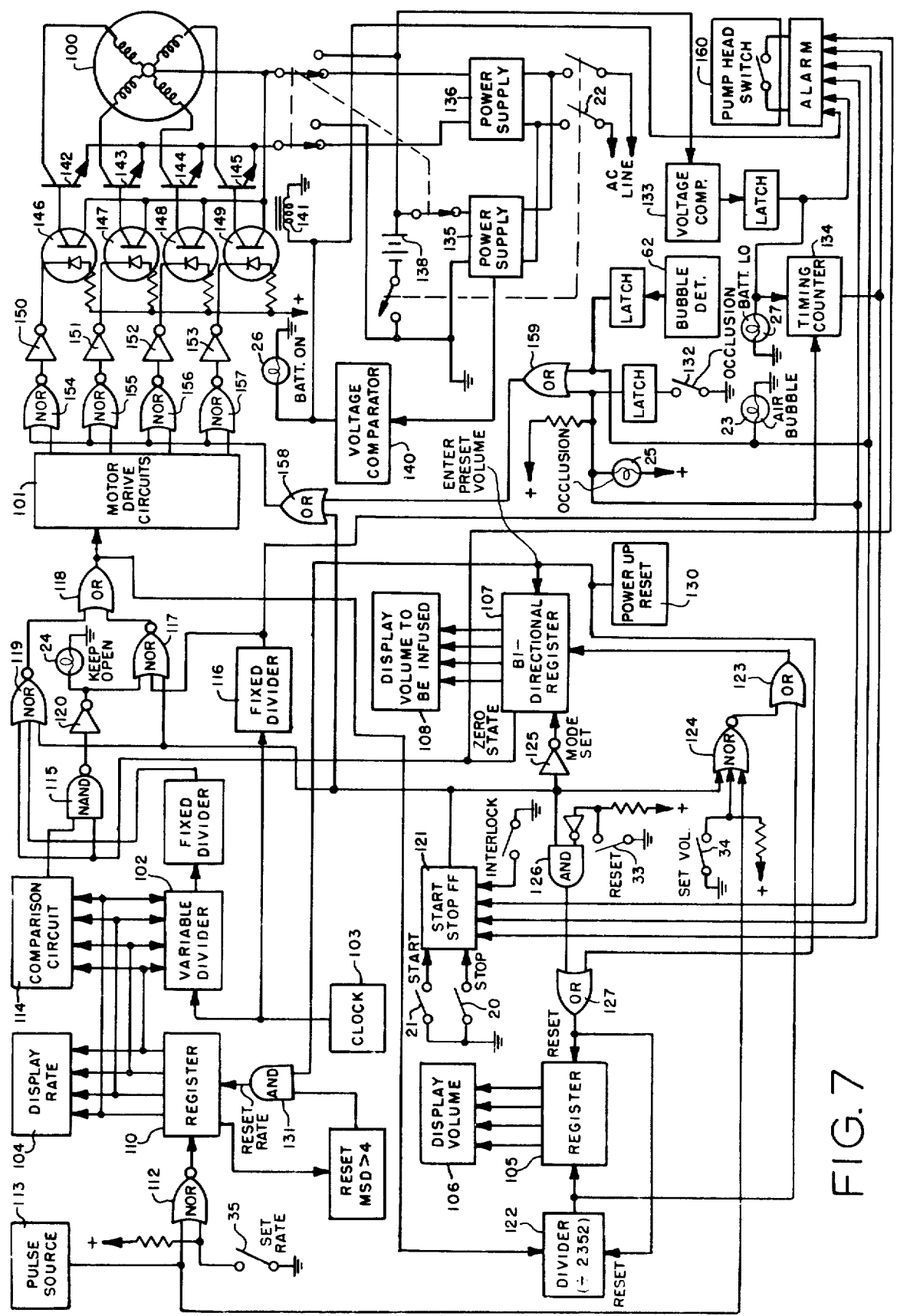
FIG. 7 is a functional block diagram partially in schematic form of the control system.

The control system of the flow metering apparatus 10 is shown in greater detail in FIG. 7. Here the division factor of variable divider 102, and hence the fluid infusion rate, is seen to depend on the counting state of a register 110. This counting state can be conveniently set by the user by means of the rate setting switches 35 which enable respective NOR gates 112 to supply pulses to the register from a pulse source 113. In practice, several NOR gates and rate setting switches are provided to allow each digit of the register to be independently set. The counting state of register 110 is displayed by display device 104 as an indication of the metering or infusion rate of the apparatus.

The output of register 110 is applied to a comparison circuit 114 wherein the register counting state is compared with a predetermined fixed minimum rate, typically 5 ml. per hour, to determine whether the infusion rate established by divider 102 is greater than or less than the minimum rate. In the event that the desired rate is greater than the minimum rate, comparison circuit 114 produces an output signal which enables NAND gate 115 to provide for establishment of a minimum "keep open" rate after the desired quantity of fluid has been infused. To this end, the output of clock 103 is applied to a fixed divider 116 which provides output pulses at a fixed minimum "keep open" rate. These pulses are applied to a NOR gate 117 and, depending on the state of this gate, to an OR gate 118 for application to the motor drive circuits 101. The "keep open" mode is operative only after the desired quantity of fluid has been infused, as signaled by the bi-directional register 107 reaching a zero counting state.

The output signal generated by register 107 upon reaching a zero counting state is applied to the remaining input of NAND gate 115 and to one input of a NOR gate 119. As a result, NOR gate 119 is inhibited and the application of pulses from variable divider 102 is interrupted. Should NAND gate 115 be enabled as a result of the variable rate being greater than the predetermined minimum flow rate, the zero state output signal from register 107 is applied through an inverter 120 to a keep open indicator 24 and to an input of NOR gate 117, wherein it serves as an enabling signal. This gate, when enabled, allows the fixed rate pulses from the fixed rate divider 116 to be applied to OR gate 118, and hence to motor drive circuits 101. In this way, a minimum flow rate is maintained even after the desired quantity has been infused.

To provide start-stop control over stepper motor 100 the remaining inputs of NOR gates 117 and 119 are connected to the output of a start-stop flip-flop 121. This flip-flop may be conditioned to a start state by actuation of the push button START switch 21, or to a stop state by actuation of the push button STOP switch 20, or by occurrence of any one of a number of abnormal conditions, including interruption of power, detection of a bubble in the administration set, detection of an occlusion in the administration set, or the opening of the metering head pressure plate while the metering apparatus is in operation.

To provide an accurate indication of the volume of fluid actually infused, the output of OR gate 118 is applied to a fixed divider stage 122 wherein a constant division factor is applied to generate one output pulse for each milliliter of fluid infused. In practice, where stepper motor 100 is required to step 2,352 times to pump 1 milliliter through tubing segment 16, divider 122 may be set to divide by 2,352 to obtain the desired volume-indicative output signal. This output signal is applied to register 105 wherein it advances the counting state of the register so that the instantaneous counting state thereof indicates the volume of fluid actually infused. As previously stated, this volume is displayed by display device 106.

The volume-indicative output pulses from divider 122 are also applied through an OR gate 123 to the stepping input of bi-directional register 107 wherein they cause that register to count down one step toward zero with each milliliter passing through the system. As stated previously, the counting state of register 107, and hence the volume of fluid to be infused, is displayed by display device 108.

Prior to use of the infusion metering apparatus, the counting state of register 107 is preset by the user by momentarily applying pulses to the register from pulse source 113. This is accomplished through a NOR gate 124 which is enabled by the operator by actuation of the SET VOLUME switch 34. In practice, one such switch and NOR gate are provided for each decade of the counter. The remaining input of NOR gate 124 is connected to the output of the start-stop flip-flop 121 to prevent the volume display from being changed while the metering apparatus is in operation.

Register 107 is capable of counting either up or down depending on an applied mode control signal. This signal is developed from the output of start-stop flip-flop 121 by means of an inverter 125 so as to condition register 107 to count up with application of set pulses from source 113 when the apparatus is stopped, and to count down with application of volume-indicative pulses from divider 122 when the metering apparatus is in operation.

Prior to initial operation of the metering apparatus register 105 is reset by the operator by actuation of push button RESET switch 33. This switch is connected to one input of an AND gate 126, the other input of which is connected to the output of the start-stop flip-flop 121 to render the reset switch 33 non-functional while the metering apparatus is in operation. The output of AND gate 126 is applied through an OR gate 127 to the reset inputs of register 106 and divider 122. In this way, the divider and register are simultaneously reset to a zero counting state prior to initial operation of the apparatus.

An auto reset state 130 responsive to initial application of power to the apparatus is provided to automatically establish an initial counting state in registers 105, 107 and 110. The output of the auto reset stage is applied to the remaining input of OR gate 127 so as to establish a zero counting state in register 105 and divider 122, and to the reset input of register 110 through AND gate 131. Should the operator attempt to set the most significant digit of register 110 above 4, a reset circuit coupled to the remaining input of AND gate 131 also resets the register. In this way the setting of infusion rates in excess of 499 ml. per hour is prevented. The output of the auto reset stage is also applied to register 107, wherein it establishes a minimum counting stage of 1 ml. to prevent initiation of the "keep open" mode before the metering apparatus has been placed in operation.

Operation of the infusion metering apparatus is interrupted upon occurrence of an occlusion within the administration set, as detected by a switch 132 associated with plunger 67 (FIGS. 3 and 5). This switch, which may be a pressure switch similar to switches 33-35, or a magnetically-actuated Hall-effect switch, is actuated by an actuator lever attached to the plunger when the plunger is allowed to close against the tubing as a result of an occlusion within the administration set. The switch provides an output signal which actuates a latch circuit to condition start-stop flip-flop 121 to a STOP state and illuminate occlusion indicator lamp 25.

Operation of the apparatus is also interrupted in the event of a bubble being detected at bubble detector 62. In this event, an output signal is generated by the bubble detector which actuates a latch circuit to condition the start-stop flip-flop 121 to interrupt operation of the metering apparatus. At the same time, BUBBLE indicator lamp 23 is illuminated to alert the operator.

Operating power for the fluid metering apparatus is supplied by means of two unidirectional current supplies 135 and 136 which receive operating power from the AC line through ON-OFF switch 22. A battery 138 is provided as an additional source of operating power in the event of failure of the AC line. The battery is connected through switch 22 across the output of power supply 135.

Normally, battery 138 is maintained charged by power supply 135 and the various control circuits of the infusion metering apparatus are powered by this combined source, while the stepper motor 100 is powered by the power supply 136. To guard against interruption of AC line voltage the output of the power supply 135 is continuously monitored by a voltage comparator 140. Upon occurrence of a line voltage interruption an output signal is produced by comparator 140 which simultaneously illuminates a BATTERY ON indicator 26 and actuates a relay 141.

Operation of the metering apparatus is interrupted whenever the battery voltage falls below a predetermined minimum level for a predetermined period of time. To this end, the battery voltage is continuously monitored by a voltage comparator stage 133. Upon occurrence of a low voltage condition, an output signal is produced which activates a latch circuit to illuminate the BATTERY LOW lamp 27 and initiate operation of a timing counter 134. This counter counts the "keep open" output pulses developed by fixed divider 116 to obtain a 10 minute time delay. If the low voltage condition persists beyond this delay period an output signal is developed by timing counter 134 which causes the BATTERY LOW lamp to flash and conditions start-stop flip-flop 121 to interrupt operation of the metering apparatus. It should be noted that the operation of comparator 133 is entirely independent of comparator 140, and serves as a check on system voltage whether supplied by power supply 135 or battery 138.

Stepper motor 100 is powered by power supply 136 through transfer contacts on relay 141. The purpose of these contacts is to substitute battery 138 as a source of power for the stepper motor in the event of an AC line failure as detected by comparator 140. The various phase windings of motor 100 are individually supplied from power supply 136 by means of switching transistors 142–145 connected in series with the windings.

In accordance with another feature of the apparatus, isolation is obtained between stepper motor 100 and the pulse-sensitive control circuits of the metering apparatus by means of individual optical isolators 146–149 associated with respective ones of the switching transistors. Each of the optical isolators includes a light detecting element connected between the motor current source and a respective one of the switching transistors, and a light emitting diode (LED) element connected to the output of a respective one of inverting amplifiers 150–153. These amplifiers receive phase control signals from motor drive circuits 101 through respective NOR gates 154–157 which serve as a safety shutoff control means for the metering apparatus.

The NOR gates 154–157 are disabled when the start-stop flip-flop 121 is conditioned to a stop mode by means of an OR gate 158 having an output connected to one input of each of the NOR gates. Also, these NOR gates can be disabled by outputs from bubble detector 62 and occlusion switch 132 through an additional OR gate 159 which provides an additional input to OR gate 158. Thus, occurrence of an occlusion, detection of a bubble, or conditioning of the start-stop flip-flop to a stop state for any reason causes the interruption of control signals to optical isolators 146–149 and interruption of drive power to stepper motor 100.

In operation, the user initially sets an infusion rate by actuating switch 35 to apply a requisite number of pulses to register 110. The counting state of this register sets the variable divider 102 such that control pulses are developed at the output thereof with a repetition rate commensurate with the desired infusion rate. These control pulses are applied through NOR gate 119 to the motor drive circuits 101 wherein they are utilized to generate multiple phase control signals suitable for controlling the operation of the multi-phase stepper motor 100. Each of the phase signals developed by drive circuits 101 is applied through a respective one of NOR gates 154–157 and inverter amplifiers 150–153 to a respective one of optical isolators 146–149. These isolators in turn control conduction in respective ones of drive transistors 142–145 to apply current from power supply 136 to stepper motor 100. In this way, the stepper motor turns the peristaltic rotor 40 at a rate established by the operator.

To provide a continuous readout of fluid volume infused the drive pulses applied to the drive circuits 101 are also applied to divider 122 to develop pulses indicative of the number of complete milliliters infused. These pulses are counted by register 105 to provide a display in device 106 indicative of the actual quantity of fluid infused.

Prior to initial operation of the apparatus an initial counting state is established in register 107 by momentary application of pulses from pulse source 113 through NOR gate 124 and OR gate 123 to establish an initial counting state indicative of the total volume of fluid to be infused. Register 108 is conditioned to count up at this time by start-stop flip-flop 121 through inverter 125.

Once this volume is set, operation is started by actuation of switch 21 and register 107 is conditioned to count down by flip-flop 121. Pulses from divider 122 indicative of actual volume infused are now applied through OR gate 123 to count register 107 down toward zero. When the register reaches a zero counting state, indicating that the desired volume of fluid has been infused, an output signal from register 107 inhibits NOR gate 119 and prevents further operation of stepping motor 100 by pulses from the variable divider 102. However, should the rate established by variable divider 102 be greater than a predetermined minimum infusion rate, comparison circuit 114 provides an enabling signal to NAND gate 115 which allows the output signal from register 107 to enable NOR gate 117 through inverter 120. This establishes a "keep open" mode of operation wherein pulses from fixed divider 116 provide motor drive circuits 101 with stepping command signals at a frequency which maintains a desired minimum flow rate through the system.

Registers 106, 107 and 110 are automatically reset upon initial operation of the system by the auto reset circuit 130. Register 105 may also be manually reset by switch 33 when the start-stop flip-flop 121 is conditioned to a stop state.

Protection against occlusion in the administration set is provided by switch 132, which conditions flip-flop 121 to a stop state and inhibits AND gates 154–157. Similarly, protection against the formation of bubbles within the administration set is provided by bubble detector 62, which also conditions flip-flop 121 to a stop state and inhibits AND gates 154–157. Protection against AC line failure is provided by voltage comparator 140 which actuates relay 141 to switch stepper motor 100 to battery 138, and by voltage comparator 133 which interrupts operation of the apparatus upon occurrence of a low voltage condition for a predetermined period of time.

Upon occurrence of any one of the above alarm functions, or upon infusion of the desired fluid volume, an aural alarm 160 is actuated to alert the operator that attention to the apparatus is required. A switch associated with the pressure plate of the pump head locks out the alarm when the pump head is opened.

Figure 8:
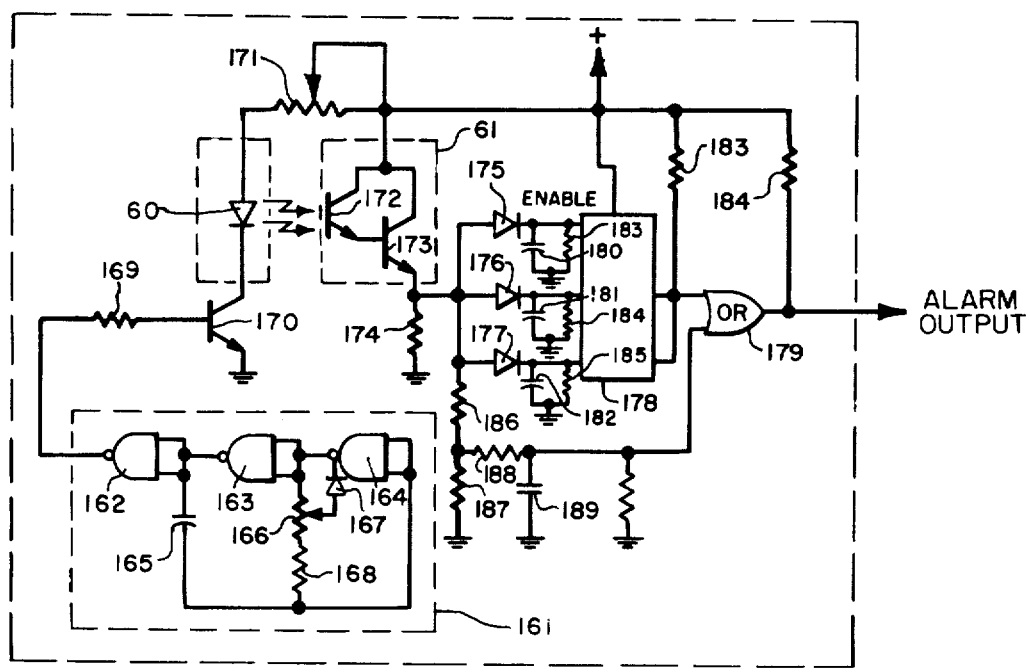
FIG. 8 is a simplified schematic diagram of the bubble detector utilized in the fluid metering apparatus of the invention.

Referring to FIG. 8, the bubble detector 62 of the infusion apparatus includes an AC-powered detection circuit which offers improved detection sensitivity and stability. Basically, the detection circuit, as shown in FIG. 8, comprises a multi-vibrator 161 consisting of three NAND gates 162, 163 and 164. A capacitor 165 connected to the output of gate 163 and a potentiometer 166 connected to the output of gate 164 provide an RC time constant which determine the frequency of the multi-vibrator output signal in a manner well known to the art. A diode 167 is connected between the arm of potentiometer 166 and the output of gate 164 to vary the duty cycle of the oscillator output signal. A fixed impedance 168 connected in series with the body of potentiometer 166 provides a desired adjustment range.

The AC signal generated by multi-vibrator 161 is applied through an impedance 169 to the base of a transistor 170. The emitter of transistor 170 is connected to ground and the collector is connected to the cathode of a light emitting diode (LED) which comprises the light source 60 disposed on one side of the administration set tubing segment 16. The anode of the LED is connected to a source of positive unidirectional current through a resistor 171. As a result, the AC signal developed by multi-vibrator 161 is amplified by transistor 170 and utilized to drive the LED, causing the LED to produce a light output which varies at a rate dependent on the output frequency of the multi-vibrator.

The alternating light developed by the LED is detected by photodetector 172 and associated amplifier transistor 173, which together comprise the light detector 61 adjacent tubing segment 16. The collectors of photodetector 172 and transistor 173 are connected to the positive unidirectional current source of the apparatus, and the emitter of detector 172 is connected to the base of transistor 173. The emitter of transistor 173 is connected to ground through a resistor 174 and through respective diodes 175–177 to respective inputs of a dual Schmitt trigger 178. The cathodes of diodes 175–177 are connected to ground by respective ones of capacitors 180–182 and resistors 183–185 in parallel circuit configuration. These elements serve in conjunction with the diodes a signal detector, generating a DC signal at the inputs of trigger 178 dependent on the amplitude of the AC signal produced by detector 61. Trigger 178, which may be a commercially available component such as a type MC14583B marketed by Motorola, produces an output upon reduction below a predetermined threshold level of the DC signal developed at either of the inputs associated with diodes 176 and 177. The input associated with diode 175 functions as an enabling input for both triggers. The output of Schmitt trigger 178 is applied to one input of an OR gate 179.

The emitter of transistor 173 is also connected to ground through series-connected resistors 186 and 187. The signal developed at the junction of the two resistors is filtered by a series-connected resistor 188 and a capacitor 189 and parallel-connected resistor connected to ground and applied to the remaining input of OR gate 179. In this way OR gate 179 is provided with the output signal developed by the two Schmitt triggers 178 and a DC control signal developed across capacitor 189, either of which can result in a bubble-indicative output from the gate in the event of a bubble occurring in tubing segment 16. The output of Schmitt triggers 178 and the output of OR gate 179 are also connected to the positive unidirectional current source of the system by respective resistors.

Since the output of OR gate 179 is dependent on both the amplitude of the AC signal as rectified and applied to the parallel-connected Schmitt triggers 178, and on the DC signal developed across capacitor 189, the bubble detector utilized in the metering apparatus provides two independent control channels. The first channel, which utilizes Schmitt triggers 178, establishes a highly precise threshold below which an alarm output is produced. The second channel, which depends only on the input characteristic of gate 179 and is less precise, serves as a backup in the event of failure of the Schmitt triggers in an active mode.

In order for bubble detector 62 to not provide an output, it is necessary that the DC signals applied to the Schmitt triggers as a result of rectification by diodes 176 and 177 be above a predetermined minimum level, which is possible only when there is fluid within tubing segment 16 which acts as a lens to direct light from light source 60 to detector 172. In the event of failure of the light source or the detector, or any other component of the system, the DC signal applied to the Schmitt triggers is removed and an alarm output is generated. In the event of failure of the Schmitt triggers, an alarm output will be developed by OR gate 179 upon loss of the DC signal from capacitor 189. The use of an AC signal eliminates drift in the circuitry as a factor affecting the threshold level of the Schmitt triggers, thereby allowing the threshold to be set closer to the normal operating level of the system for greater detection efficiency.

Transient spikes on the AC line, which are particularly prevalent in institutions such as hospitals where electrical machinery is in operation, introduce the potential of spurious counts in the digital registers and gates utilized in the control circuits of the metering apparatus. For this reason, it is imperative that the greatest possible isolation be provided by power supplies 135 and 136 between the control circuits and the AC line, particularly in view of the possibly critical life-determining nature of the metering apparatus.

Figure 9:
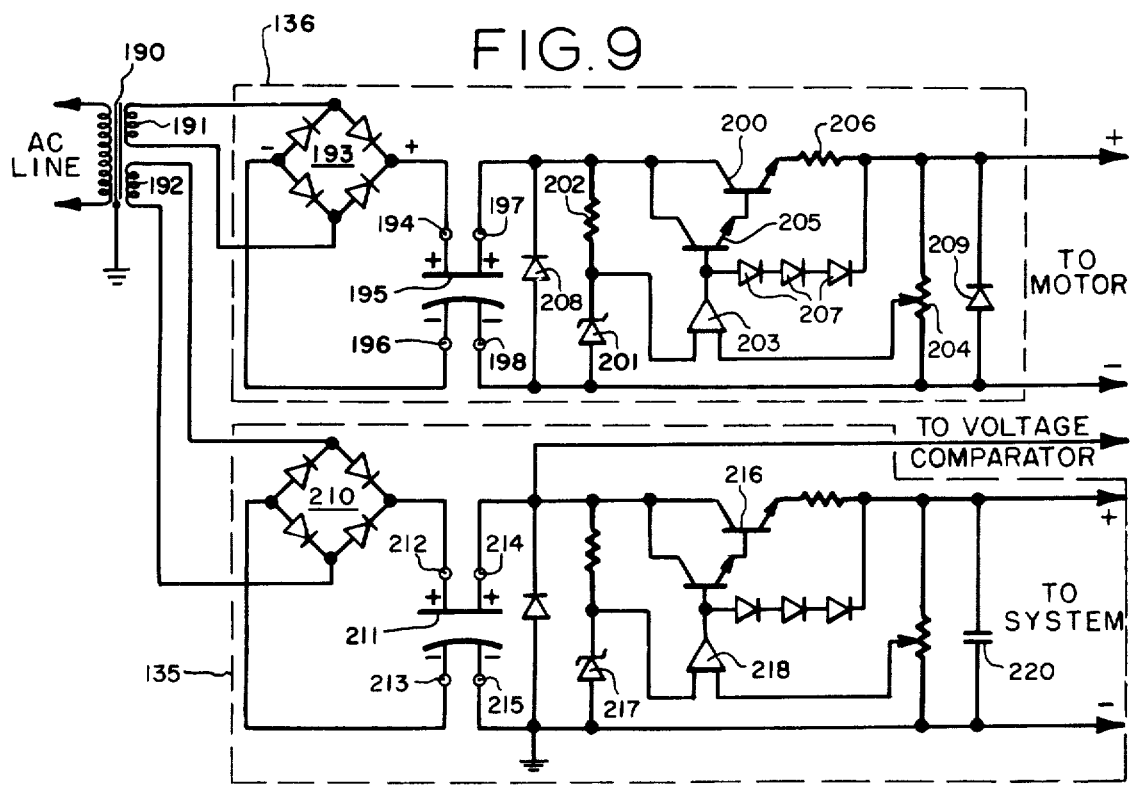
FIG. 9 is a simplified schematic diagram of the power supplies utilized in the fluid metering apparatus of the invention.

To this end, separate power supplies each incorporating special transient protection features are provided in the metering apparatus. Referring to FIG. 9, it is seen that the two power supplies 135 and 136 share a common power transformer 190 which includes individual secondary windings 191 and 192 each electrostatically shielded from the line. The output of secondary winding 191 is connected across a bridge rectifier 193 within power supply 136. The positive polarity output of bridge rectifier 193 is connected to the positive polarity input terminal 194 of a first four-terminal filter capacitor 195. The negative input terminal 196 of this capacitor is connected to the negative polarity output of the bridge rectifier.

Filter capacitor 195 is an electrolytic type capacitor which includes four terminals; a first pair of terminals associated with respective ends of the positive plate of the capacitor, and a second pair of terminals associated with respective ends of the negative or foil side of the capacitor.

The output terminals 197 and 198 of capacitor 195 are connected to a conventional voltage regulator circuit which includes a series-connected regulator transistor 200. In a manner well known to the art, the conduction state of transistor 200 is varied in response to the voltage level existing at the output of power supply 136 so as to maintain the voltage level constant. To this end, a zener diode 201 and resistor 202 are connected across the output electrodes of the capacitor to develop a reference voltage. This reference voltage is compared within a comparator amplifier 203 with a portion of the output voltage of the power supply as developed by a potentiometer 204 connected across the output terminals of the supply. The output of comparator 203, representing the deviation of the output voltage from a reference level, is applied to a transistor 205 which serves to amplify the error signal prior to application to the base of transistor 200. Additional regulation to compensate for changes in current load is provided by a series-connected resistor 206 at the emitter of transistor 200. This register develops an additional error signal which is applied through three series-connected voltage dropping diodes 207 to the base of the error amplifier transistor 205. Protection against transient spikes is provided by reverse-biased diodes 208 and 209 connected across the input and output leads of the voltage regulator, respectively.

Power supply 135, which is virtually identical to power supply 136, includes a bridge rectifier 210 connected across secondary winding 192, and a four terminal filter capacitor 211 having input terminals 212 and 213 connected across the output of the bridge rectifier. The output terminals 214 and 215 of the capacitor are connected to a series regulator circuit similar to that contained in power supply 136, including a series regulator transistor 216, a voltage reference zener diode 217 and a differential amplifier 218 with similar functions. A filter capacitor 220 is connected across the output of the power supply to provide additional filtering.

The described power supply arrangement has the advantage of providing a high degree of filtering between the AC line and the respective power supply busses of the metering apparatus. The four-terminal filter capacitors are particularly effective in this respect, in that any transient currents attempting to enter or leave the respective power supplies must pass through the electrodes of the capacitor, since these electrodes are relied upon to complete the metallic circuit. As a result, the filtering action of the capacitors is not reduced with transients of higher frequencies, as in conventional filter capacitors.

The use of separate power supplies, each utilizing the four-terminal filter capacitor component, provides a very high degree of isolation between the stepper motor circuit and the digital control circuitry of the metering apparatus. This is desirable because of the relatively high switching transients inherent in the operation of a stepper motor, and the possibility of these transients affecting the critical digital control circuitry.

Thus, the invention provides a flow metering apparatus for fluid infusion systems which allows the operator to directly select fluid flow rate and volume without the need for calculations. The apparatus is convenient to install and does not require particular skills on the part of the operator for its operation. Protection is provided within the apparatus against malfunctions in the administration set and with the apparatus itself, in the event of which the operator is signaled and operation of the apparatus is terminated. The apparatus is portable and of a construction which lends itself to convenient use in a hospital environment.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

We claim:

1. Metering apparatus for controlling the flow of fluid through a fluid infusion set, comprising:
    a housing;
    a rotor mounted on said housing for rotation about a fixed axis, said rotor including a plurality of pressure rollers disposed about the circumference thereof;
    means including a pressure plate for positioning a tubing segment of the administration set in compressive engagement with at least a portion of said rollers whereby fluid is pumped through said tubing segment with rotation of said rotor;
    means including a stepper motor for driving said rotor;
    first motor control means for generating stepping pulses at a first predetermined rate for controlling the rotation of said stepper motor to obtain a desired flow rate through said tubing segment;
    second motor control means for generating stepping pulses at a second predetermined rate for maintaining a desired minimum flow rate through said tubing segment;
    volume totalizer means including a register responsive to said stepping pulses for interrupting application of stepping pulses from said first motor control means and initiating application of stepping pulses from said second motor control means to said stepper motor upon passage of a desired volume of fluid through said tubing segment; and
    inhibiting means responsive to the flow rate established by said first motor control means for inhibiting operation of said second motor control means when said predetermined rate is less than a predetermined maximum rate.

2. Metering apparatus as defined in claim 1 wherein said predetermined maximum rate corresponds to said second predetermined rate.

3. Metering apparatus as defined in claim 1 including a source of clock pulses, and wherein said first and second motor control means include respective first and second registers responsive to said clock pulses for producing said stepping pulses upon occurrence of respective predetermined numbers of said clock pulses, the predetermined number of pulses required by said first register is variable to establish a desired infusion rate, and wherein said inhibiting means is responsive to the requirement of said first register.

4. Metering apparatus as defined in claim 3 wherein said requirement of said first register is dependent on the counting state of a third register, and said inhibiting means is responsive to the counting state of said third register.

5. Metering apparatus for controlling the flow of fluid through a fluid infusion set, comprising:
    flow control means operatively associated with a tubing segment of the infusion set and responsive to applied control pulses for producing an incremental flow of predetermined volume through the infusion set upon occurrence of each control pulse;
    first rate control means for generating control pulses at a first predetermined rate for controlling the operation of said flow control means to obtain a desired flow rate through said tubing segment;
    second rate control means for generating control pulses at a second predetermined rate for controlling the operation of said flow control means to maintain a desired minimum flow rate through said tubing segment;
    volume totalizer means including a register responsive to said control pulses for interrupting application of control pulses from said first rate control means and initiating application of control pulses from said second rate control means to said flow control means upon passage of a desired volume of fluid through said tubing segment; and
    inhibiting means responsive to the flow rate established by said first rate control means for inhibiting operation of said second rate control means when said predetermined rate is less than a predetermined maximum rate.

6. Metering apparatus as defined in claim 5 wherein said predetermined maximum rate corresponds to said second predetermined rate.

7. Metering apparatus as defined in claim 5 including a source of clock pulses, and wherein said first and second rate control means include respective first and second registers responsive to said clock pulses for producing said control pulses upon occurrence of respective predetermined numbers of said clock pulses, the predetermined number of pulses required by said first register is variable to establish a desired infusion rate, and wherein said inhibiting means is responsive to the requirement of said first register.

8. Metering apparatus as defined in claim 7 wherein said requirement of said first register is dependent on the counting state of a third register, and said inhibiting means is responsive to the counting state of said third register.

9. Metering apparatus operable in an environment subject to liquid spillage for controlling the flow of fluid through a fluid infusion set, comprising:
- a housing substantially sealed against entry of said spilled liquid;
- flow control means mounted on said housing operatively associated with a tubing segment of the infusion set and responsive to applied control pulses for producing an incremental flow of predetermined volume through the infusion set upon occurence of each control pulse;
- rate control means for generating control pulses for application to said flow control means, each of said control pulses providing a flow of predetermined incremental volume through said tubing segment;
- a bi-directional register;
- means for interrupting the operation of said flow control means upon said register reaching a predetermined reference counting state;
- volume preset means comprising a source of repetitive pulses, and user-actuable momentary action switch means for applying said pulses to said register, for causing said bi-directional register to count up to establish an initial counting state in said register prior to initial actuation of said flow control means; and
- means for applying said control pulses to said bi-directional register to cause said register to count down in response to said control pulses whereby said register reaches said reference counting state upon a desired volume of fluid being infused through the infusion set.

10. Fluid metering apparatus as defined in claim 9 wherein said reference counting state comprises a zero counting state, and wherein display means responsive to the counting state of said bi-directional counter are provided for indicating the volume of fluid remaining to be infused by the apparatus.

11. Fluid metering apparatus as defined in claim 9 wherein said user-actuable switch means comprise an inwardly-deformable section of said housing, said switch being mounted within said housing in operative engagement with said housing whereby said switch is actuated with user-initiated deformation of said housing section.

* * * * *